United States Patent
Mills (10) Patent No.: US 9,927,377 B2
(45) Date of Patent: Mar. 27, 2018

(54) AGRICULTURAL SIZER WITH ITEM STABILIZER BELT

(71) Applicant: Daniel G. Mills, Acampo, CA (US)

(72) Inventor: Daniel G. Mills, Acampo, CA (US)

(*) Notice: Subject to any disclaimer, the term of this patent is extended or adjusted under 35 U.S.C. 154(b) by 0 days.

(21) Appl. No.: 15/221,564

(22) Filed: Jul. 27, 2016

(65) Prior Publication Data
US 2018/0031494 A1    Feb. 1, 2018

(51) Int. Cl.
| | | |
|---|---|---|
| *B07C 1/04* | (2006.01) | |
| *G01N 23/02* | (2006.01) | |
| *B07C 5/04* | (2006.01) | |
| *G01N 33/02* | (2006.01) | |
| *G01N 33/10* | (2006.01) | |
| *B65G 15/14* | (2006.01) | |

(52) U.S. Cl.
CPC .............. *G01N 23/02* (2013.01); *B07C 1/04* (2013.01); *B07C 5/04* (2013.01); *B65G 15/14* (2013.01); *G01N 33/025* (2013.01); *G01N 33/10* (2013.01); *B07C 2501/0081* (2013.01)

(58) Field of Classification Search
CPC .. B07C 5/02; B07C 5/04; B07C 5/344; B07C 2501/009; B65G 15/14; B65G 15/16; B65G 2201/0211
USPC ................. 198/626.1, 626.2, 626.6; 209/589
See application file for complete search history.

(56) References Cited

U.S. PATENT DOCUMENTS

| | | | |
|---|---|---|---|
| 2,813,617 A * | 11/1957 | Sheetz ..................... | A23N 3/00 198/415 |
| 3,446,332 A | 4/1969 | Bechtloff | |
| 3,882,995 A | 5/1975 | Uraya | |
| 4,195,724 A | 4/1980 | Janitsch | |
| 4,482,061 A * | 11/1984 | Leverett ................... | B07C 5/18 198/384 |
| 5,052,543 A * | 10/1991 | Hagan .................. | B65G 47/244 198/387 |
| 5,121,635 A * | 6/1992 | Coffelt ..................... | A23N 3/00 198/385 |
| 5,305,868 A | 4/1994 | Grathoff | |
| 5,428,657 A * | 6/1995 | Papanicolopoulos | G01N 23/20083 378/86 |
| 5,472,080 A * | 12/1995 | Fukuoka ................ | B65G 15/12 193/37 |
| 5,847,382 A | 12/1998 | Koch | |
| 5,865,291 A * | 2/1999 | Affeldt ................... | B65G 47/24 198/460.1 |

(Continued)

*Primary Examiner* — Joseph C Rodriguez
(74) *Attorney, Agent, or Firm* — R. Michael West (57) ABSTRACT

A sizing apparatus has input and output ends and a sampling window therebetween. Sizing means determines the size of each item passing through the sampling window. Singulating means arranges the items in a line and delivers them sequentially at the input end of the sizing apparatus. A lower conveyor belt extends through the sizing apparatus from the input end through the sampling window to the output end. The lower conveyor belt is translated at a speed sufficient to receive, transport, and maintain the items in sequential fashion. A flexible upper stabilizer belt is arranged above and generally in alignment with the lower conveyor belt, and is driven to match the speed of the lower conveyor belt. The upper stabilizer belt is suspended so as to engage the items incoming from said singulating means and to maintain loose contact with them until the items have passed through the sampling window.

20 Claims, 5 Drawing Sheets

(56) References Cited

U.S. PATENT DOCUMENTS

| | | | |
|---|---|---|---|
| 6,170,637 B1 * | 1/2001 | Ishii | B65G 47/22 |
| | | | 198/443 |
| 6,401,913 B1 * | 6/2002 | Blanc | B07C 5/02 |
| | | | 198/387 |
| 6,655,878 B1 * | 12/2003 | de Vos | A23N 3/00 |
| | | | 406/198 |
| 7,311,191 B2 * | 12/2007 | Bahr | B65G 47/2445 |
| | | | 198/396 |
| 7,793,773 B2 * | 9/2010 | Beck | B65G 39/125 |
| | | | 198/571 |
| 8,061,503 B2 * | 11/2011 | Ancarani | B65G 47/2445 |
| | | | 198/398 |
| 8,683,903 B2 * | 4/2014 | Strong | B23D 47/045 |
| | | | 198/626.4 |
| 9,475,643 B1 * | 10/2016 | Odman | B65G 37/005 |
| 9,580,874 B2 * | 2/2017 | Millsaps, II | B60P 1/36 |
| 9,670,006 B2 * | 6/2017 | Ruigrok | B65G 47/24 |
| 2007/0179662 A1 | 8/2007 | Erlingsson | |

\* cited by examiner

AGRICULTURAL SIZER WITH ITEM STABILIZER BELT

BACKGROUND OF THE INVENTION

1. Field of the Invention

The invention relates generally to apparatus for accurately determining the size of agricultural comestibles and performing sorting operations based upon those determinations. More specifically, the invention pertains to an agricultural sizer provided with an improved apparatus for stabilizing food items during the period when they are sampled by X-Ray irradiation, for size and other characteristics.

2. Description of the Prior Art

U.S. Pat. No. 5,847,382 issued to Koch et al., discloses a Bone Detector. This device includes a flexible clear plastic lower conveyor to transport deboned poultry. A fluorescent bulb illuminates the passing food product from below. An upper conveyor belt has a portion which runs parallel to and in spaced relation from the lower conveyor. The upper conveyor is made from a plurality of linked rigid plastic slats which bear down on the poultry to reduce its thickness during the bone detection process, improving the accuracy of bone detection.

In Patent Application Publication US 2007/0179662, filed by Erlingsson et al., a device is taught which uses X-Ray emissions to detect bone fragments, rather than a visible light spectrum illuminator. At least one roller 5 is used alone or in combination with a belt 6, to compress the meat or chicken piece 3, to the desired thickness when it is irradiated with X-Rays.

U.S. Pat. No. 5,305,868, granted to Grathoff, illustrates a Cover Belt Conveyor. This device comprises a cover belt 2 and a basic belt 1, in which at least one of these belts is driven. A delivery strand 4 is formed in the central portion of these belts. Elastic support rollers 6 impress upon at least the cover belt 2. Reinforcements 3 are provided on at least one of the belts, and they are effective laterally to confine objects within the delivery strand 4. The support rollers 6 are "elastically" mounted to maintain the cover belt 2 for translation while carrying objects.

A Belt Conveyor is shown in U.S. Pat. No. 3,882,995, issued to Uraya. A pair of endless belts, partly contacting each other, is employed to provide a conveying passage. Opposing sides of the belts are entirely covered with hook and loop VELCRO® like surfaces, so they are in mating engagement unless an object 15 intervenes. As shown in FIG. 1, spring-biased rollers translate laterally to accommodate the additional thickness of transported objects as they pass between the rollers.

In U.S. Pat. No. 3,446,332, granted to Bechtloff, a Steep Conveyor Installation is taught. This arrangement uses foam material on opposing surfaces, some of which include convolutions. FIG. 3 shows a conveying system having an input end and an output end, in which the foam surfaces are in contact with each other from the time the conveyed objects enter the system to the time they are discharged.

A Belt Elevator With Staggered Edge Roller is disclosed in U.S. Pat. No. 4,195,724, granted to Janitsch. This apparatus employs a plurality of drive and idler pulleys to maintain a pair of belts in encompassing, gripping relation around the granular bulk material, during its transport.

However, the need still exists for improved means for stabilizing but not damaging or compressing food products, as they are passed through an apparatus which can determine their size and other characteristics, for subsequent sorting.

The need also exists for a system for transporting food items, which is radiolucent at X-Ray frequencies and which maintains the food items in stable relation as they are irradiated for sampling.

The need further exists for an apparatus which suppresses and eliminates erratic and non-linear motion of food items being delivered from an item singulator to a sizing apparatus.

The need further exists for an apparatus which is simple and inexpensive to retrofit to an existing sizing apparatus to improve its efficiency, accuracy, and reliability in making size, shape, weight, and defect determinations of harvested comestibles.

These and other objects and features of the invention herein will become apparent from the drawings and the written specification which follow.

SUMMARY OF THE INVENTION

The sizing apparatus disclosed herein has an input end, and output end, and a sampling window therebetween. The sizing apparatus includes sizing means for determining at least the size of each item passing through the sampling window. Preferably, the sizing means comprises an X-Ray source and a plurality of detectors, along with a computer and software for analyzing the data provided by the sampling process. The computer makes item size determinations, and provides a delayed output signal to actuate a downstream item sorting apparatus. Using the same data, other determinations about the item's characteristics can also be made, such as the shape, weight, and presence or lack of defects in the item sampled. Although the sizing apparatus as described is designed to size and sort agricultural comestibles, it may also be adapted for use in sorting applications for other types of items.

Upstream singulating means is provided, for preliminarily arranging items to be sized in a line and delivering them sequentially at the input end of the sizing apparatus. The singulator described herein includes a plurality of rotatably driven rods defining each side of an inclined trough through which incoming items pass. The plurality of rods on one side of the trough has their axes of rotation arranged in parallel relation, downwardly inclined and converging with respect to the plurality of rods on the other side of the trough. Drive belts in contact with the undersides of the rods, are used to rotate the rods on each side, respectively, in a direction toward the lower end of the trough. The forces from frictional contact with the rotating surface of the rods in combination with the forces of gravity, urge the items to travel downwardly in the trough, resulting in sequential, lineal delivery of the items to the input end of the sizing apparatus.

A lower conveyor belt extends through the sizing apparatus from the input end through the sampling window to at least the output end. The segment of the lower conveyor belt passing through the sizing apparatus is V-shaped in cross-section, having a lower portion and upwardly diverging sidewall portions. The V-shaped configuration for the segment of the lower conveyor belt is effected by a rigid V-shaped belt trough, which underlies and supports the belt segment, shaping its form.

The lower conveyor belt is driven at a speed which is sufficient to receive and transport the items delivered by the upstream singulator, and to maintain the items in lineal sequential relation as they are passed through the sizing apparatus. If the speed is too slow, incoming items may collect and bunch at the input end, causing the items to lose their sequential, lineal arrangement. If the speed is too fast, the items may roll and bounce on the lower conveyor belt, again causing loss of the desired sequential, lineal arrangement.

An upper stabilizer belt is further provided, to maintain the items in a secure relation on the lower conveyor belt, particularly as each item passes through the sampling window. The upper stabilizer belt is arranged above and generally in alignment with the lower conveyor belt. The upper stabilizer belt is flexible and is driven at a speed to match the speed of the lower conveyor belt, so they will move in unison.

The upper stabilizer belt is suspended at both ends in such a manner as to engage the items incoming from the upstream singulator. If the items are bouncing or moving about as they are about to enter the sizing apparatus, the upper stabilizer belt suppresses this undesirable action and movement. The upper stabilizer belt further maintains loose contact with the items, until they have at least passed through the sampling window. This dampening effect ensures that the images of the items obtained by the sampling means, will be sharp and accurate. Accurate image data for an item, in turn, ensures that the determinations made about that item will also be accurate, and that the effectiveness of sorting actions based on those determinations will be improved.

Also disclosed is an item sorting apparatus, located downstream from the sizing apparatus, for processing the items as needed. Using the item image data obtained by the sizing means, the items may be processed and graded with respect to a number of characteristics, including size, shape, weight, and internal defects. The sorting apparatus receives control signals from the computer based upon the image data for an item, and then physically acts upon that item after it emerges from the output end of the sizing apparatus. In that manner, an item is grouped with other items having identical or similar characteristics. An item may also be returned to the input end of the sizing apparatus for re-sampling, or if determined to have an internal defect, it may be rejected and removed from the item stream.

DETAILED DESCRIPTION OF THE PREFERRED EMBODIMENT

Figure 1:
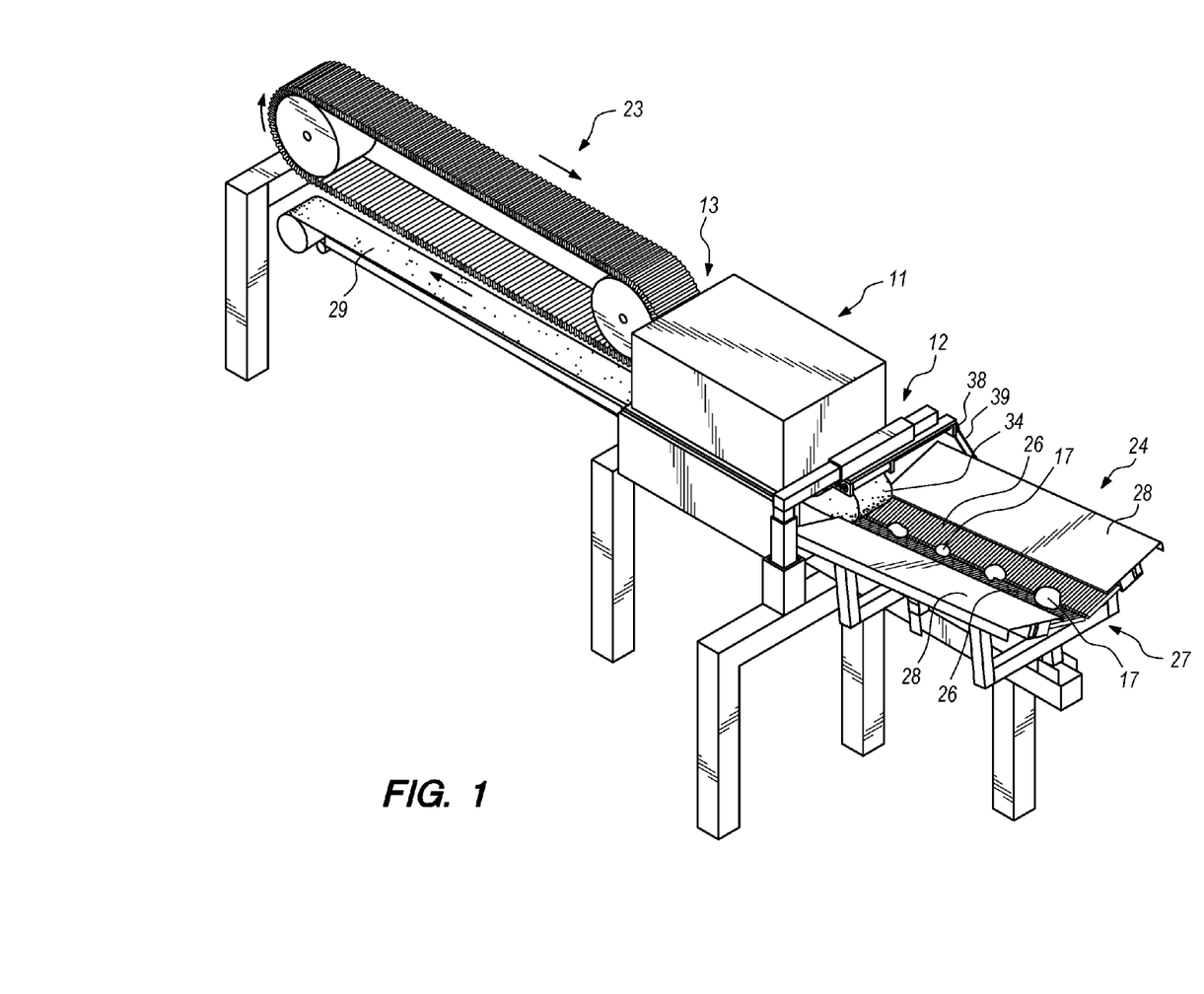
FIG. 1 is an elevated perspective view of a singulator, a sizing apparatus, and an item sorting apparatus.
Figure 4:
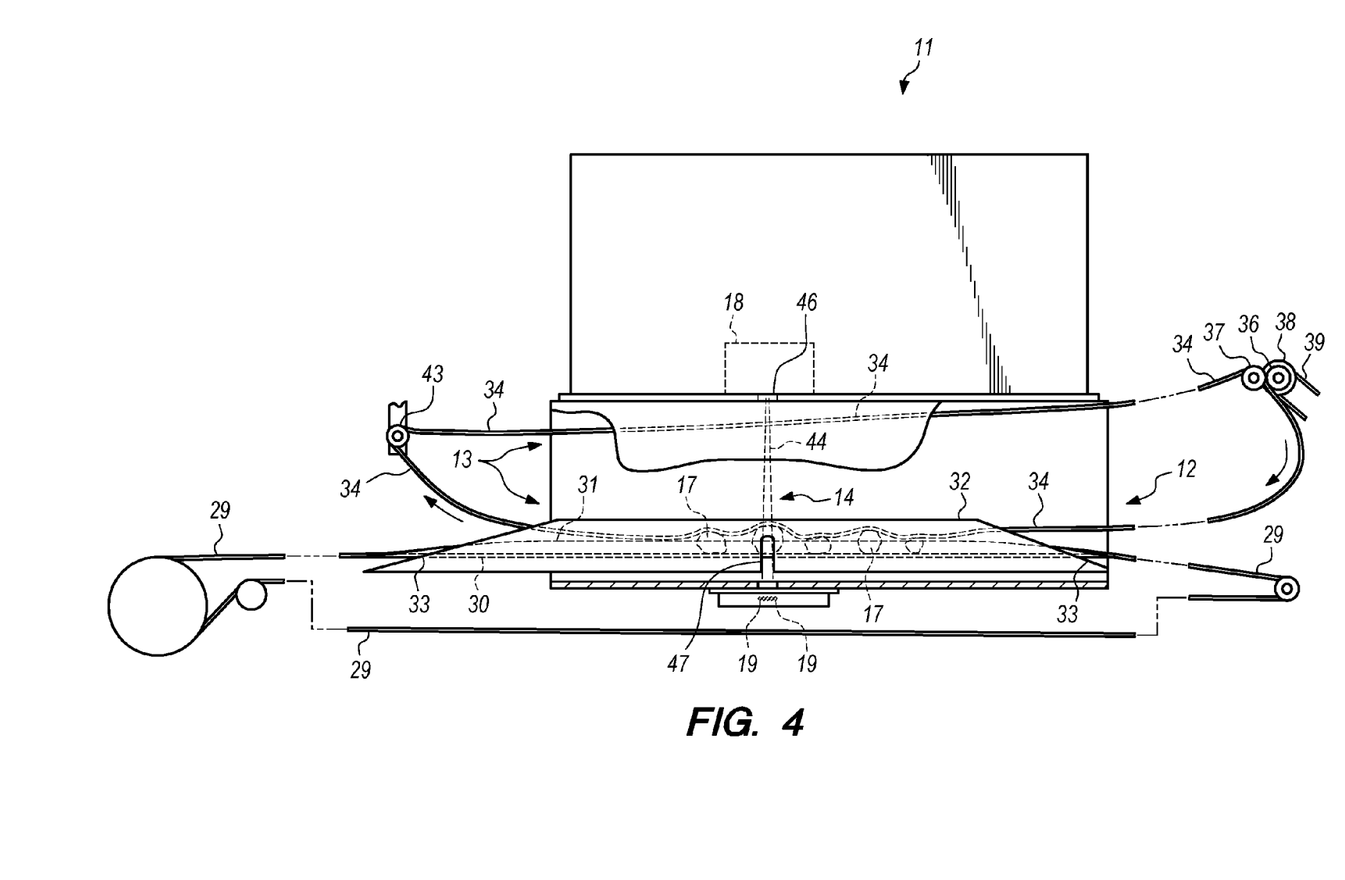
FIG. 4 is a side elevational view of the sizing apparatus, showing the lower conveyor belt, the upper stabilization belt, and portions of the sizing means in broken line.

Turning now to FIGS. 1 and 4, the sizing apparatus 11 has an input end 12, an output end 13, and a sampling window 14 therebetween. The sizing apparatus 11 includes sizing means 16, shown in FIG. 5, for determining at least the size of each item 17 passing through the sampling window 14. Preferably, the sizing means 16 comprises an X-Ray source 18 and a plurality of detectors 19, along with a computer 21 and associated software for analyzing the data provided by the sampling process for each item 17.

Figure 5:
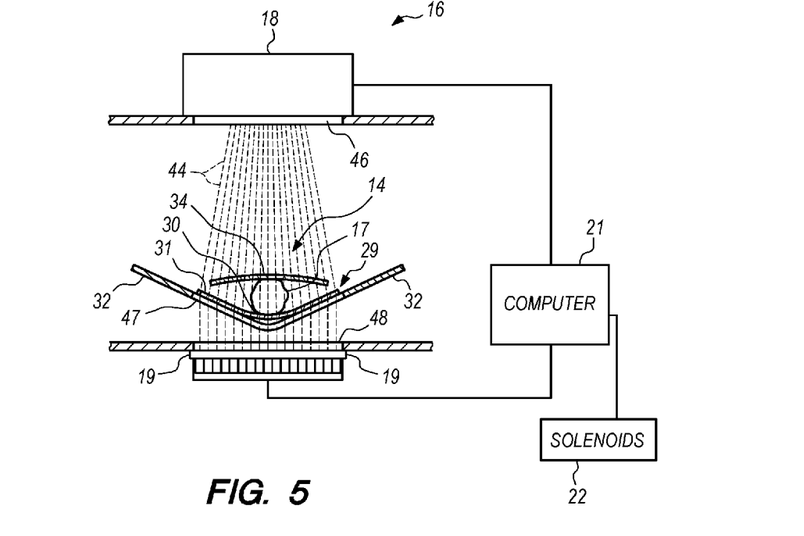
FIG. 5 is a fragmentary cross-section view, taken on the line 5-5 in FIG. 3, showing in order, the X-ray source, the upper stabilization belt, an item in the sampling window, the lower conveyor belt, the belt trough, and the X-ray detectors.

The X-Ray source 18 is a low powered X-Ray generator, which produces synchronous pulses of energy in concert with control signals from computer 21. The Spellman company of Hauppauge, N.Y., manufactures suitable X-Ray sources for this application. The plurality of detectors 19 is oriented transversely, with respect to the direction of travel of each item 17. In that manner, successive "slices" of the item 17 are exposed and detected, and item image data is outputted to computer 21. This data is analyzed by computer 21 in synchronism with the control signals producing corresponding pulses of energy from X-Ray source 18.

Figure 2:
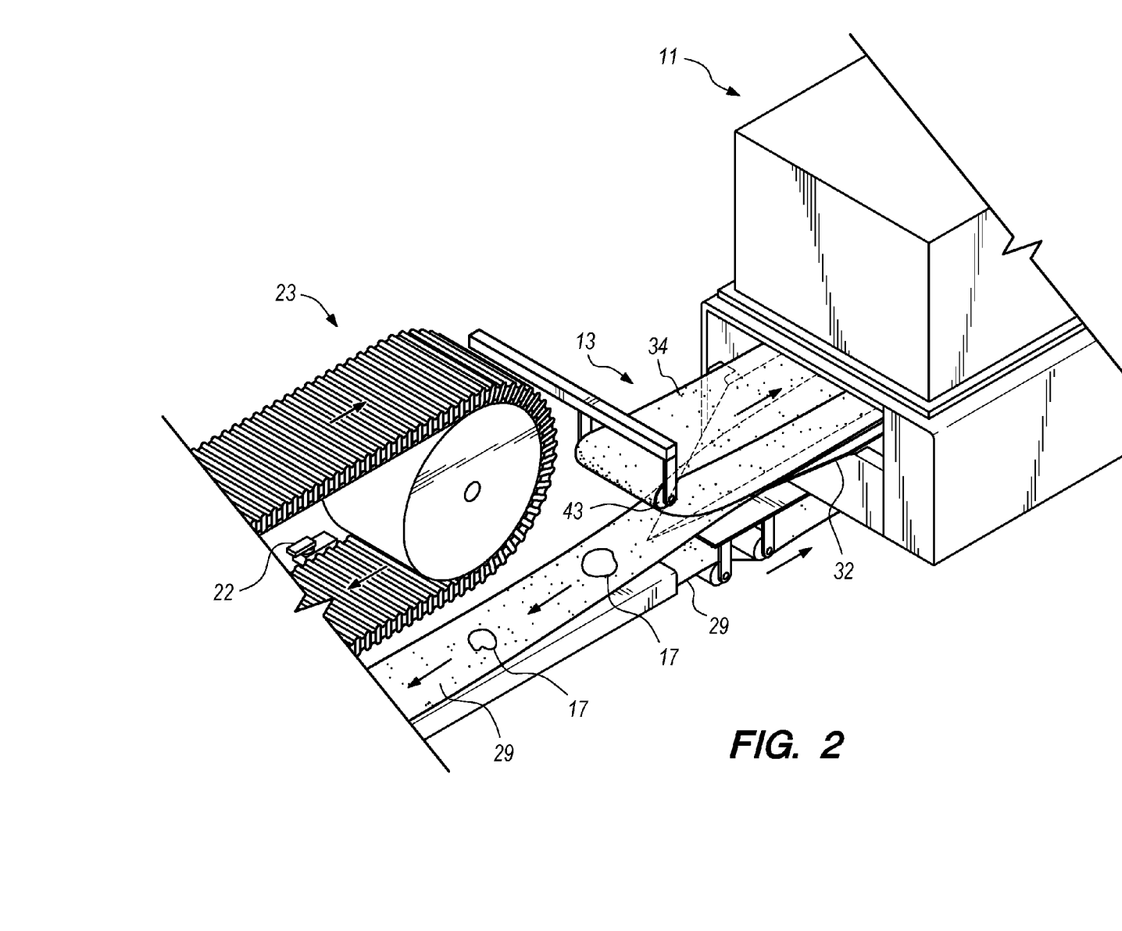
FIG. 2 is a fragmentary perspective view of the output end of the sizing apparatus, showing one end of the upper stabilization belt.

The computer 21 makes at least item size determinations, and provides a delayed output signal to actuate one or more solenoids 22 in a downstream item sorting apparatus 23 (See, FIG. 2), to be described in more detail below. It is important to note that by using the same item image data, other determinations can also be made such as the shape, weight, and presence or lack of defects in the item 17 sampled. In other words, the sizing apparatus 11 in reality, typically does much more than "size" each item 17.

For example, a grower or food processor may desire to sort oblong potatoes from round potatoes. That is accomplished by defining predetermined shape characteristics in the software algorithms, so that appropriate determinations and downstream sorting can be accomplished. Or, for purposes of subsequent packaging, it may be more efficient to separate all items 17 under 8 ounces from those items 17 over 8 ounces. With the item size data at hand, by also using the density of the item 17 determined by the relative strength of the detected X-Ray pulses, such weight determinations can be made. Lastly, a grower or food processor will likely want to remove items 17 having an internal defect from the stream of items 17. Internal defective conditions such as hollows or "black heart", will cause density readings to vary outside predetermined parameters, triggering a reject determination by the computer 21.

The sizing apparatus 11 described herein is designed to size and sort agricultural comestibles, such as nuts, fruits, berries, carrots, garlic, and potatoes. The sizing apparatus 11 has also been tested with other agricultural products, and with the appropriate software for computer 21, can make many different and varied sorting decisions. However, it may also be adapted for use in sorting applications for other types of items 17 which are not comestibles, but which have characteristics that influence or affect X-Ray irradiation. These changes in the detected X-Ray irradiation may include the divergence from a predetermined signal intensity, or the convergence with a predetermined pattern, or a similar trigger mechanism. In these cases, the sizing apparatus 11 may well be adapted for other sorting applications.

Upstream singulating means 24 is provided, for preliminarily arranging the items 17 in a line and delivering them sequentially at the input end 12 of the sizing apparatus 11. See, FIGS. 1 and 3. The singulator 24 described herein includes a plurality of rotatably driven rods 26, defining each side of an inclined trough 27 through which incoming items 17 pass. The respective pluralities of rods 26 on each side of the trough 27 have their axes of rotation arranged in parallel relation. The rods 26 on one side of the trough 27 are oriented downwardly, to converge with the plurality of rods 26 on the other side of the trough 27. Inclined side plates 28, are located on each side of the trough 27 of the singulator 24, with their lower edges slightly overlapping the upper end of the rods 26. Side plates 28 are effective to restrain items 17 which may bounce around within trough 27, and to reintroduce such items 17 to the singulating action of the rods 26.

Figure 3:
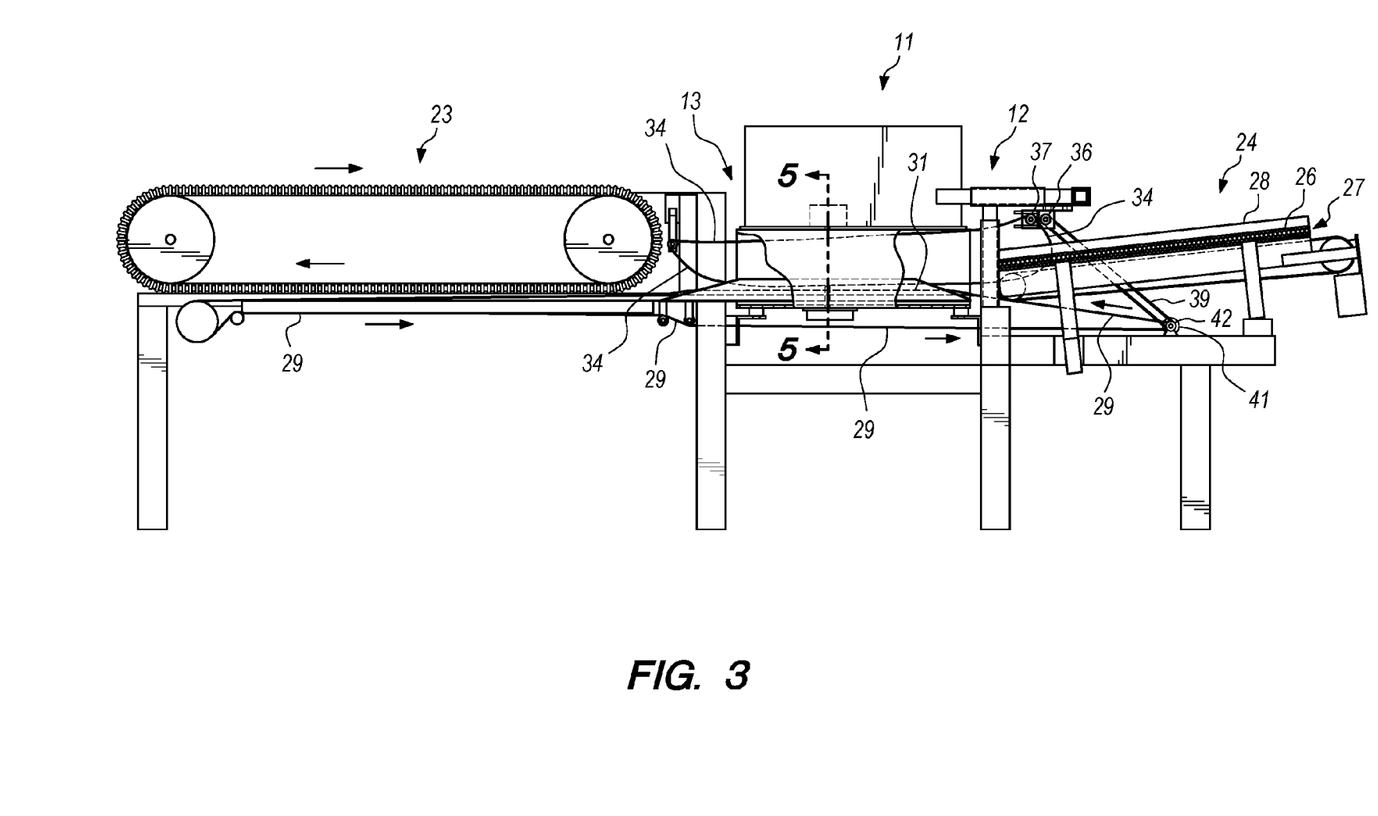
FIG. 3 is a side elevational view of the singulator, the sizing apparatus, and the item sorting apparatus, a portion of the sidewall of the sizing apparatus being broken away to show the belt trough and the upper stabilization belt.

Drive belts (not shown), which are in contact with the undersides of the rods 26, are used to rotate the rods 26 on each side in a direction toward the lower end of the trough 27. The rotating surfaces of the rods 26 create frictional contact with each of the items 17. These forces, in combination with the forces of gravity, urge the items 17 to travel downwardly in the trough 27. This results in sequential, lineal delivery of the items 17 to the input end 12 of the sizing apparatus 11.

An endless lower conveyor belt 29 extends through the sizing apparatus 11 from the input end 12 through the sampling window 14 to at least the output end 13. As shown in FIGS. 1 and 3, lower conveyor belt 29 may also be conveniently extended to the downstream end of item sorting apparatus 23, thereby eliminating the need for a separate conveyor for apparatus 23. When it passes through sizing apparatus 11, lower conveyor belt 29 is V-shaped in cross-section having a lower portion 30 and upwardly diverging sidewall portions 31. See, FIGS. 4 and 5. The V-shaped configuration for this segment of the lower conveyor belt 29 is effected by a rigid V-shaped belt trough 32, preferably made from steel. Trough 32 includes tapered and curved end portions 33, which transition belt 29 from a flat belt into a V-shaped belt segment and back into a flat belt.

Lower conveyor belt 29 is driven at a speed which is sufficient to receive and transport the items 17 delivered by the upstream singulator 24, and to maintain the items 17 in lineal, sequential relation as they are passed through the sizing apparatus 11. It is apparent that if the speed of belt 29 is too slow, incoming items 17 may collect and bunch at input end 12, causing the items to lose the sequential, lineal arrangement necessary for separate sampling of each item 17. It should also be apparent that if the speed of belt 29 is too fast, items 17 may roll and bounce on the portion of lower conveyor belt 17 within sizing apparatus 11, again causing loss of the desired sequential, lineal arrangement necessary for individual item sampling.

An endless upper stabilizer belt 34 is provided to maintain items 17 securely on the lower conveyor belt 29, particularly as each item 17 passes through the sampling window 14. Stabilizer belt 34 is made from a soft and flexible material, preferably a synthetic such as polyester or nylon. As will be described below, belt 34 is so loosely suspended in its lower run that it gently drapes over items 17, without compressing or otherwise damaging even the most delicate comestible. See, FIGS. 4 and 5.

The upper stabilizer belt 34 is arranged above and generally in alignment with the lower conveyor belt 29. At the upstream end of belt 34, a drive roller 36 and a pinch roller 37 are provided. Drive roller 36 includes a pulley 38 which is engaged by a drive belt 39. The lower end of drive belt 39 engages a pulley 41, provided on lower conveyor belt roller 42. In that manner, upper stabilizer belt 34 is driven at a speed to match the speed of the lower conveyor belt 29, so they will move in unison.

Upper stabilizer belt 34 extends around pinch roller 37, passing between pinch roller 37 and drive roller 36. The longitudinal axis of pinch roller 37 is adjustable with respect to the longitudinal axis of drive roller 36. When rollers 36 and 37 are sufficiently close frictionally to engage belt 34, belt 34 will be driven the desired speed. As is shown most clearly in FIG. 2, upper stabilizer belt 34 is supported at its downstream end by an idler roller 43. The lower run of stabilizer belt 34 is loosely suspended between pinch roller 37 and idler roller 43, with a certain amount of slack at both ends. As a consequence, the forward portion of stabilizer belt 34 directly engages items 17 incoming from singulator 24. If items 17 are bouncing or sliding around as they are about to enter the sizing apparatus 11, the upper stabilizer belt 34 suppresses this undesirable action and movement.

The lower run of the upper stabilizer belt 34 further maintains loose contact with the items 17, until they have at least passed through the sampling window 14. This dampening effect ensures that the images of the items 17 obtained by the sizing means 16, will be sharp and accurate. Accurate image data for an item, in turn, ensures that the determinations made about that item will also be accurate, and that the effectiveness of sorting actions based on those determinations will be improved.

Figure 6:
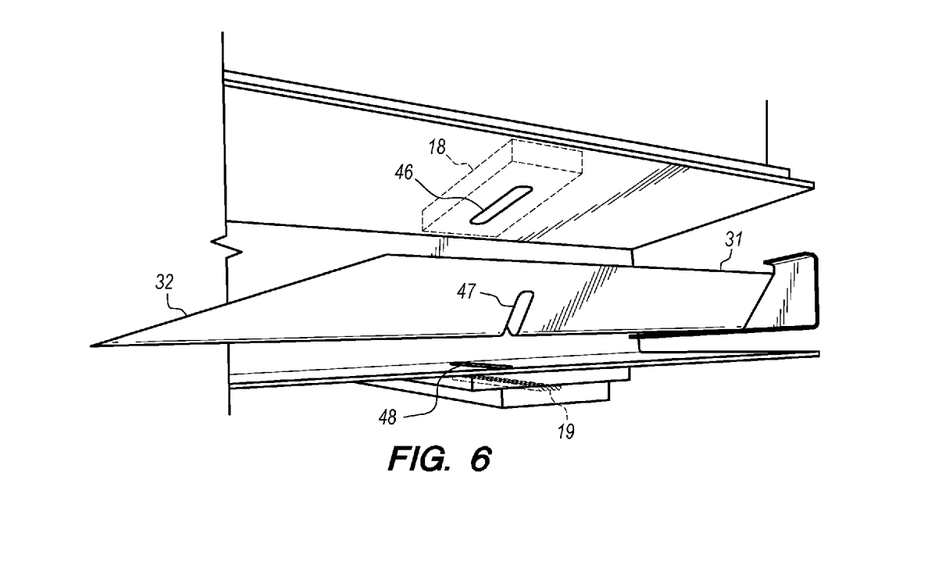
FIG. 6 is a fragmentary perspective view of the X-ray source housing, the belt trough, and the X-ray detector housing.

This image gathering process is best understood with reference to FIGS. 4 and 5. As the items 17 progress through sizing apparatus 11, they sequentially enter and exit sampling window 14. Upper stabilizer belt 34 is draped over item 17, moving at the same speed as lower conveyor belt 29. Although being moved at the speed of belts 29 and 34, item 17 is maintained in stable relation with respect to both belts. X-Ray source 18 produces X-Ray pulses 44 which pass through upper slot 46, upper stabilizer belt 34, item 17, lower conveyor belt 29, a trough slot 47, a lower slot 48, and then impinge upon detectors 19. See, FIGS. 5 and 6.

The output from detectors 19 is fed into computer 21. Software associated with computer 21, stores and analyzes the item image data, and makes various determinations, based upon the pre-programmed criteria and algorithms. Computer 21 then appropriately outputs a control signal to one or more solenoids 22 made part of item sorting apparatus 23.

Item sorting apparatus 23, located downstream from sizing apparatus 11, processes and sorts the items 17 with respect to a number of characteristics, including size, shape, weight, and internal defects. Item sorting apparatus 23 is made in accordance with the teachings of the corresponding apparatus shown in U.S. Pat. No. 6,380,503. The entirety of U.S. Pat. No. 6,380,503 (the '503 patent) is hereby incorporated by reference. In particular, FIGS. 1, 2, and 10-15, of the '503 patent and the associated textual portions, show the features and explain the operation of a sorting apparatus which can readily be adapted by a person of ordinary skill in the art, for use with the present invention to perform item sorting. For that reason, no further explanation or details regarding item sorting apparatus 23 will be provided, as the '503 patent provides such a teaching.

The item sorting apparatus 23 receives control signals from the computer 21 based upon the image data for an item 17, and then physically acts upon that item 17 after it emerges from the output end 13 of the sizing apparatus 11. In that manner, an item 17 is grouped with other items 17 having identical or similar characteristics. An item 17 may also be returned to the input end 12 of the sizing apparatus 11 for re-sampling, or if determined to have an internal defect, it may be rejected and removed from the item stream.

What is claimed is:

1. An apparatus for determining the size of items, comprising:
   a. a sizing apparatus having an input end, and output end, and a sampling window therebetween, said sizing apparatus including sizing means for determining size for each item passing through said sampling window;

b. singulating means for arranging items in a line and delivering them sequentially at said input end of said sizing apparatus;

c. a rigid V-shaped belt trough extending through said sizing apparatus from said input end to said output end, said belt trough including tapered and curved end portions;

d. a flexible lower conveyor belt, said lower conveyor belt having a segment lying within and being formed by said belt trough, said segment of said lower conveyor belt being V-shaped in cross-section having a lower portion and upwardly diverging sidewall portions, said tapered and curved end portions of said belt trough transitioning said lower conveyor belt from a flat belt into a V-shaped belt segment and back into a flat belt, said lower conveyor belt being translated at a speed sufficient to receive and transport the items delivered by said singulating means in sequential fashion; and, e. an upper stabilizer belt, said upper stabilizer belt being arranged above and generally in alignment with said lower conveyor belt, said upper stabilizer belt further being flexible and driven to match said speed of said lower conveyor belt, said upper stabilizer belt being suspended so as to engage the items incoming from said singulating means and to maintain loose contact with them until the items have passed through said sampling window.

2. The apparatus of claim 1 in which said sizing means uses X-Ray irradiation to determine the size of items.

3. The apparatus of claim 2 in which the items are agricultural comestibles, including nuts, fruits, berries, carrots, garlic, and potatoes.

4. The apparatus of claim 1 in which said singulating means comprises a plurality of rotatably driven rods defining each side of an inclined trough, said plurality of rods on each side having their axes arranged in parallel relation and inclined downwardly and converging with respect to the rods comprising the other side.

5. The apparatus of claim 1 in which said lower conveyor belt and said upper stabilizer belt are endless and driven together.

6. The apparatus of claim 1 in which said upper stabilizer belt is driven and supported at said input end of said sizing apparatus by a drive roller and a pinch roller, said upper stabilizer belt being frictionally engaged between said drive roller and said pinch roller, and in which said upper stabilizer belt is supported at said output end of said sizing apparatus by an idler roller.

7. The apparatus of claim 6 in which said drive roller is coupled to a lower conveyor belt drive.

8. The apparatus of claim 1 in which said upper stabilizer belt is made from a polyester or nylon fabric.

9. The apparatus of claim 1 including sorting means downstream from said output end of said sizing apparatus, said sorting means being responsive to an output signal from said sizing apparatus and effective to act upon individual items exiting from said output end and direct them to a collection container for other items having an identical or similar size.

10. An apparatus for determining the size of items, comprising:

a. a sizing apparatus having an input end and an output end, said input end being adapted for receiving items delivered sequentially in a line;

b. a rigid V-shaped belt trough extending through said sizing apparatus from said input end to said output end;

c. a flexible lower conveyor belt, said lower conveyor belt having a segment lying within and being formed by said belt trough, said segment being V-shaped in cross-section having a lower portion and upwardly diverging sidewall portions, said lower conveyor belt thereby being configured to receive the items delivered at said input end and to transport them sequentially in a line until outputted from said output end;

d. sizing means for determining a size for each item passing through said sizing apparatus, said sizing means being located between said input end and said output end; and, e. an upper stabilizer belt, said upper stabilizer belt being arranged above and generally in alignment with said lower conveyor belt, said upper stabilizer belt further being flexible and suspended so as to engage each item incoming at said input end and to maintain loose contact with it until its size has been determined by said sizing means.

11. The apparatus of claim 10 in which said sizing means uses X-Ray irradiation to determine the size of items.

12. The apparatus of claim 10 in which the items are agricultural comestibles, including nuts, fruits, berries, carrots, garlic, and potatoes.

13. The apparatus of claim 10 in which said upper stabilizer belt is driven and supported at said input end of said sizing apparatus by a drive roller and a pinch roller, said upper stabilizer belt being frictionally engaged between said drive roller and said pinch roller, and in which said upper stabilizer belt is supported at said output end of said sizing apparatus by an idler roller.

14. The apparatus of claim 13 in which said drive roller is coupled to a lower conveyor belt drive.

15. An apparatus for determining the size of items, comprising:

a. a sizing apparatus having an input end, and output end, and a sampling window therebetween, said sizing apparatus including sizing means for determining a size for each item passing through said sampling window;

b. an item singulator including a plurality of rotatably driven rods defining each side of an inclined trough, said plurality of rods on each side having their axes arranged in parallel relation and inclined downwardly and converging with respect to the rods comprising the other side, said singulator being effective for arranging items in a line and delivering them sequentially at said input end of said sizing apparatus;

c. a rigid V-shaped belt trough extending through said sizing apparatus from said input end to said output end;

d. a flexible lower conveyor belt, said lower conveyor belt having a segment lying within and being formed by said belt trough, said segment being V-shaped in cross-section having a lower portion and upwardly diverging sidewall portions, said lower conveyor belt being translated at a speed sufficient to receive and transport the items delivered by said item singulator in sequential fashion; and, e. upper stabilizing means, said upper stabilizing means being arranged above and generally in alignment with said lower conveyor belt, said upper stabilizing means being suspended so as to engage each item incoming from said item singulator and to maintain loose contact with it until each item has passed through said sampling window.

16. The apparatus of claim 15 in which said upper stabilizing means comprises a flexible belt.

17. The apparatus of claim 16 in which said flexible belt is driven at said speed said lower conveyor belt is translated.

18. The apparatus of claim 17 in which said flexible belt is driven and supported at said input end of said sizing apparatus by a drive roller and a pinch roller, said flexible belt being frictionally engaged between said drive roller and said pinch roller, and in which said flexible belt is supported at said output end of said sizing apparatus by an idler roller.

19. The apparatus of claim 17 in which said drive roller is coupled to a lower conveyor belt drive.

20. The apparatus of claim 15 in which said sizing means uses X-Ray irradiation to determine the size of items.

* * * * *